United States Patent
Just et al.

(10) Patent No.: US 10,219,861 B2
(45) Date of Patent: *Mar. 5, 2019

(54) CATHETER ELECTRODE ASSEMBLIES AND METHODS OF CONSTRUCTION THEREOF

(71) Applicant: St. Jude Medical, Atrial Fibrillation Division, Inc., St. Paul, MN (US)

(72) Inventors: Dale E. Just, Minneapolis, MN (US); Troy T. Tegg, Elk River, MN (US); Theodore A. Johnson, St. Paul, MN (US); Sacha C. Hall, Aventura, FL (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 11 days.

This patent is subject to a terminal disclaimer.

(21) Appl. No.: 15/601,777

(22) Filed: May 22, 2017

(65) Prior Publication Data
US 2017/0319270 A1    Nov. 9, 2017

Related U.S. Application Data

(63) Continuation of application No. 14/712,694, filed on May 14, 2015, now Pat. No. 9,687,297, which is a
(Continued)

(51) Int. Cl.
*A61B 5/042* (2006.01)
*A61B 18/14* (2006.01)
*A61B 18/00* (2006.01)

(52) U.S. Cl.
CPC ........ *A61B 18/1492* (2013.01); *A61B 5/0422* (2013.01); *A61B 2018/00083* (2013.01);
(Continued)

(58) Field of Classification Search
None
See application file for complete search history.

(56) References Cited

U.S. PATENT DOCUMENTS

| 4,365,639 A | 12/1982 | Goldreyer |
| 4,890,623 A | 1/1990 | Cook et al. |

(Continued)

FOREIGN PATENT DOCUMENTS

| EP | 1442719 | 8/2004 |
| WO | 2004112629 | 12/2004 |

(Continued)

*Primary Examiner* — Kennedy Schaetzle
(74) *Attorney, Agent, or Firm* — Dykema Gossett PLLC

(57) ABSTRACT

A family of catheter electrode assemblies includes a flexible circuit having a plurality of electrical traces and a substrate; a ring electrode surrounding the flexible circuit and electrically coupled with at least one of the plurality of electrical traces; and an outer covering extending over at least a portion of the electrode. A non-contact electrode mapping catheter includes an outer tubing having a longitudinal axis, a deployment member, and a plurality of splines, at least one of the plurality of splines comprising a flexible circuit including a plurality of electrical traces and a substrate, a ring electrode surrounding the flexible circuit and electrically coupled with at least one of the plurality of electrical traces; and an outer covering extending over at least a portion of the ring electrode. A method of constructing the family of catheter electrode assemblies is also provided.

17 Claims, 7 Drawing Sheets

Related U.S. Application Data continuation of application No. 14/038,078, filed on Sep. 26, 2013, now Pat. No. 9,037,264, which is a continuation of application No. 12/958,992, filed on Dec. 2, 2010, now Pat. No. 8,560,086.

(52) U.S. Cl.
CPC .............. *A61B 2018/00267* (2013.01); *A61B 2018/00351* (2013.01); *A61B 2018/00577* (2013.01); *A61B 2018/00875* (2013.01); *A61B 2018/1407* (2013.01); *A61B 2018/1465* (2013.01); *Y10T 29/49204* (2015.01)

(56) References Cited

U.S. PATENT DOCUMENTS

| | | | |
|---|---|---|---|
| 5,429,130 A | 7/1995 | Goldman | |
| 5,456,254 A | 10/1995 | Pietroski et al. | |
| 5,499,981 A * | 3/1996 | Kordis ................. | A61B 5/0422 606/41 |
| 5,542,928 A | 8/1996 | Evans et al. | |
| 5,928,228 A | 7/1999 | Kordis et al. | |
| 5,957,900 A | 9/1999 | Ouchi | |
| 6,014,579 A | 1/2000 | Pomeranz et al. | |
| 6,097,976 A | 8/2000 | Yang et al. | |
| 6,104,944 A | 8/2000 | Martinelli | |
| 6,231,543 B1 | 5/2001 | Hegde et al. | |
| 6,233,476 B1 | 5/2001 | Strommer et al. | |
| 6,319,251 B1 | 11/2001 | Tu et al. | |
| 6,454,775 B1 | 9/2002 | Demarais et al. | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 6,945,956 B2 | 9/2005 | Waldhauser et al. | |
| 6,945,977 B2 | 9/2005 | Demarais et al. | |
| 7,197,354 B2 | 3/2007 | Sobe | |
| 7,263,397 B2 | 8/2007 | Hauck et al. | |
| 7,289,843 B2 | 10/2007 | Beatty et al. | |
| 7,386,339 B2 | 6/2008 | Strommer et al. | |
| 7,536,218 B2 | 5/2009 | Govari et al. | |
| 8,103,327 B2 | 1/2012 | Harlev et al. | |
| 8,376,991 B2 | 2/2013 | Kauphusman et al. | |
| 8,560,086 B2 * | 10/2013 | Just ...................... | A61B 5/0422 600/374 |
| 9,037,264 B2 * | 5/2015 | Just ...................... | A61B 5/0422 600/374 |
| 9,339,331 B2 | 5/2016 | Tegg et al. | |
| 9,687,297 B2 * | 6/2017 | Just ...................... | A61B 5/0422 |
| 2002/0038139 A1 * | 3/2002 | Wessman ................. | A61N 1/05 607/122 |
| 2002/0111618 A1 | 8/2002 | Stewart et al. | |
| 2002/0165535 A1 * | 11/2002 | Lesh .................. | A61B 17/2202 606/41 |
| 2002/0165537 A1 | 11/2002 | Kelley et al. | |
| 2003/0050637 A1 | 3/2003 | Maguire et al. | |
| 2003/0097094 A1 | 5/2003 | Ouriel et al. | |
| 2004/0030331 A1 | 2/2004 | Thomas et al. | |
| 2005/0033136 A1 * | 2/2005 | Govari ................. | A61B 5/0422 600/374 |
| 2005/0060885 A1 * | 3/2005 | Johnson ............... | A61B 5/0422 29/846 |
| 2005/0065508 A1 | 3/2005 | Johnson et al. | |
| 2005/0272975 A1 | 12/2005 | McWeeney et al. | |
| 2007/0083194 A1 | 4/2007 | Kunis et al. | |
| 2007/0219551 A1 | 9/2007 | Honour et al. | |
| 2008/0161801 A1 | 7/2008 | Steinke et al. | |
| 2009/0036961 A1 | 2/2009 | Chong et al. | |
| 2009/0171274 A1 | 7/2009 | Harlev et al. | |
| 2010/0094279 A1 | 4/2010 | Kauphusman et al. | |
| 2010/0117659 A1 | 5/2010 | Osadchy et al. | |
| 2010/0168647 A1 | 7/2010 | Tegg et al. | |

FOREIGN PATENT DOCUMENTS

| | | |
|---|---|---|
| WO | 2005032362 | 4/2005 |
| WO | 2008045938 | 4/2008 |

* cited by examiner

CATHETER ELECTRODE ASSEMBLIES AND METHODS OF CONSTRUCTION THEREOF

CROSS-REFERENCE TO RELATED APPLICATIONS

This application is a continuation of U.S. application Ser. No. 14/712,694, filed 14 May 2015 (the '694 application), which is a continuation of U.S. application Ser. No. 14/038,078, filed 26 Sep. 2013 (the '078 application), now U.S. Pat. No. 9,037,264, which is a continuation of U.S. application Ser. No. 12/958,992, filed 2 Dec. 2010 (the '992 application), now U.S. Pat. No. 8,560,086. The '694 application, '078 application, and the '992 application are each hereby incorporated by reference as though fully set forth herein.

BACKGROUND OF THE INVENTION a. Field of the Invention

This invention relates to the design and manufacture of a family of catheter electrode assemblies for use in cardiac procedures.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes or both. Once at the intended site, treatment may include radio frequency (RF) ablation, cryoablation, laser ablation, chemical ablation, high-intensity focused ultrasound-based ablation, microwave ablation, etc. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents stray errant conduction signals that can form the basis for arrhythmias. As readily apparent, such diagnosis and therapy delivery requires precise control of the electrophysiology catheter during manipulation to, from, and at a target tissue site for diagnostic and therapy delivery. Diagnostic maps of activation wavefronts and ectopic foci and various pathological and non-pathological conduction pathways can be stored and available to later access during therapy delivery.

BRIEF SUMMARY OF THE INVENTION

It can be desirable for the catheter electrode assembly to be sufficiently flexible so as to be delivered to the areas or volumes of target tissue(s) of interest within a patient's body. It is also desirable to increase the available surface area of at least one electrode on the catheter electrode assembly and to ensure that at least one electrode on the catheter electrode assembly is configured to face in a preferred direction (i.e., toward cardiac target tissue in the case of so-called contact therapy delivery and diagnostic catheters and away from such target tissue in the case of so-called non-contact mapping catheters).

According to this disclosure a catheter electrode assembly includes a flexible circuit having a plurality of electrical traces and a substrate; a ring electrode surrounding the flexible circuit and electrically coupled with at least one of the plurality of electrical traces; and an outer covering extending over at least a portion of the electrode. In an embodiment, a portion of the outer covering can be removed to expose at least a portion of the electrode. The electrode may connect with the electrical trace via an electrical pad on the flexible circuit. The catheter electrode assembly may further include a liner tube extending within at least a portion of the electrode.

In an embodiment, the catheter electrode assembly may further include a support member, such as a Nitinol member or more complex spine, and/or a radio opaque marker disposed within a portion of the liner tube.

The catheter electrode assembly may include a plurality of ring electrodes disposed along the length of the flexible circuit. Each ring electrode may surround the flexible circuit and can be electrically coupled with at least one of the plurality of electrical traces.

One type of electrophysiology catheter may comprise a non-contact electrode mapping catheter. The non-contact electrode mapping catheter may comprise a basket catheter including an outer tubing having a longitudinal axis, a deployment member, and a plurality of splines. Each spline may comprise a catheter electrode assembly. The catheter electrode assembly may include a flexible circuit having a plurality of electrical traces and a substrate. It can be desirable to fully encapsulate the flexible circuit to protect the flexible circuit, while still allowing a portion of an electrode that is electrically connected to the flexible circuit to be exposed. The catheter electrode assembly may further comprise a ring electrode surrounding the flexible circuit and electrically coupled with at least one of the plurality of electrical traces; and an outer covering extending over at least a portion of the ring electrode.

A method of constructing a catheter electrode assembly may include the steps of connecting an electrode to a flexible circuit; placing the flexible circuit and the electrode over a liner tube; placing an outer covering over at least a portion of the electrode, at least a portion of the flexible circuit, and at least a portion of the liner tube; and bonding at least a portion of the outer covering to at least a portion of the liner tube.

DETAILED DESCRIPTION OF EMBODIMENTS OF THE INVENTION

Figure 1:
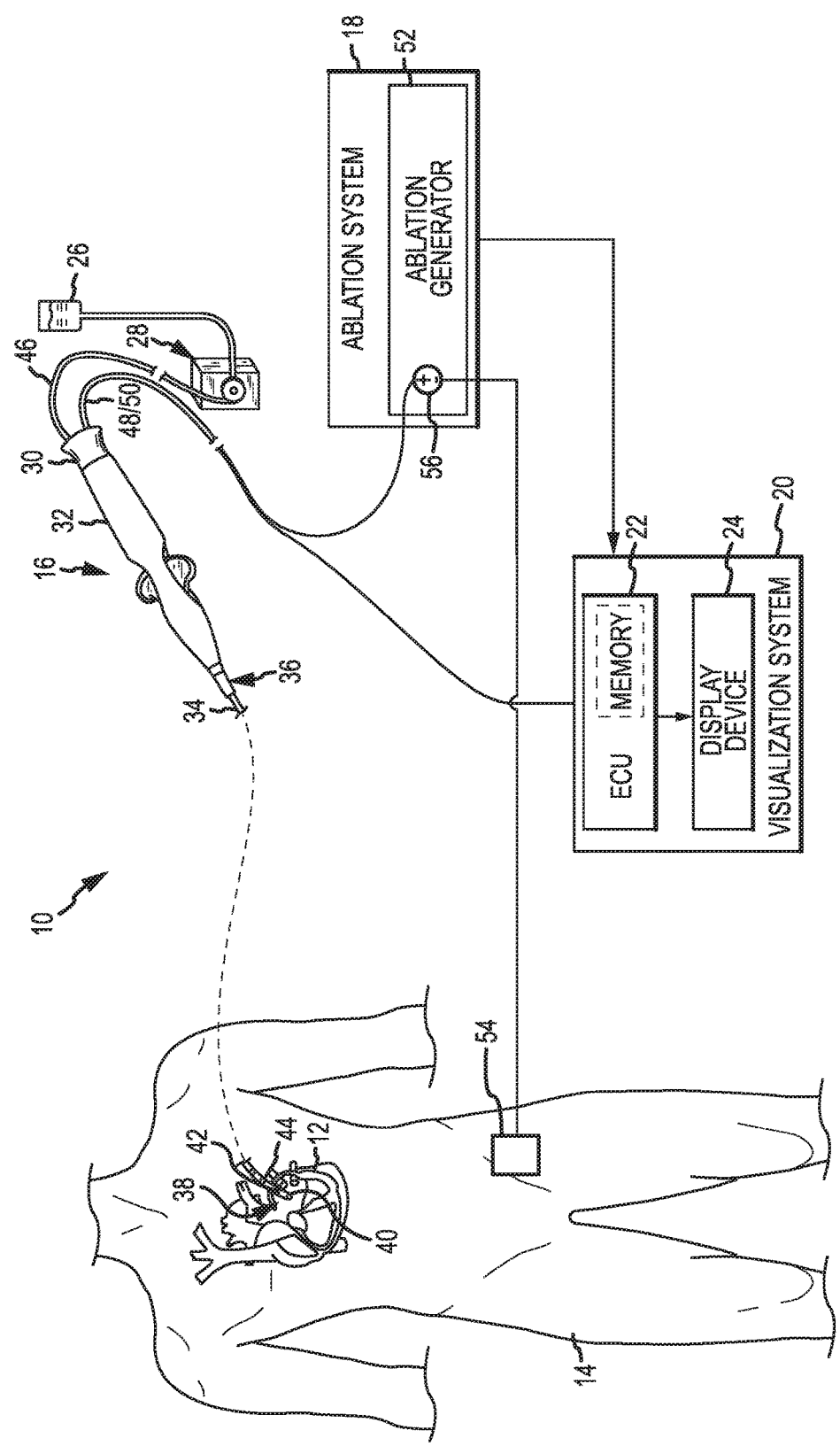
FIG. 1 is a diagrammatic view of a system for performing one more diagnostic and/or therapeutic functions in association with cardiac tissue.

Referring now to the drawings wherein like reference numerals are used to identify identical components in the various views, FIG. 1 illustrates one exemplary embodiment of a system 10 for performing one more diagnostic and/or therapeutic functions in association with the heart or cardiac tissue 12 within a human body 14. It should be understood, however, that the system 10 may find application in connection with the ablation of a variety of other tissues within human and non-human bodies.

The system 10 may include a medical device (such as, for example, an electrophysiology catheter 16) an ablation system 18, and/or a system 20 for the visualization, navigation, and/or mapping of internal body structures. The system 20 may include, for example and without limitation, an electronic control unit (ECU) 22 and a display device 24. Alternatively, the ECU 22 and/or the display 24 maybe separate and distinct from, but electrically connected to and configured for communication with, the system 20.

With continued reference to FIG. 1, the catheter 16 can be provided for examination, diagnosis, and/or treatment of internal body tissues such as the tissue 12. In an exemplary embodiment, the electrophysiology catheter 16 comprises a diagnostic catheter, such as a non-contact electrical mapping catheter that may include a plurality of electrodes configured to monitor one or more electrical signals transmitted throughout the adjacent tissue 12. For example, electrophysiology catheter 16 may comprise a non-contact electrode basket catheter. The basket catheter may comprise outer tubing, a deployment member, and a plurality of splines. The non-contact electrode basket catheter can be irrigated in an embodiment such that the catheter 16 may further comprise an inner fluid delivery tubing that may include at least one fluid delivery port (e.g., within and/or at the junction of splines or at the splines themselves of the basket catheter). In the exemplary embodiment wherein the catheter 16 is an irrigated catheter, the catheter 16 can be connected to a fluid source 26 providing a biocompatible fluid such as saline, or a medicament, through a pump 28 (which may comprise, for example, a fixed rate roller pump or variable volume syringe pump with a gravity feed supply from the fluid source 26, as shown) for irrigation. It should be understood, however, that catheter 16 is not limited to a non-contact electrical mapping catheter (e.g., non-contact electrode basket catheter) and is not limited to an irrigated catheter. Rather, in other embodiments, the catheter 16 may comprise an ablation catheter (e.g., radio frequency (RF), cryoablation, ultrasound, etc.) with or without fluid delivery through the catheter.

In an exemplary embodiment where the catheter comprises an ablation catheter, the catheter 16 is electrically connected to the ablation system 18 to allow for the delivery of ablative energy, or the like. The catheter 16 may include a cable connector or interface 30, a handle 32, a shaft 34 having a proximal end 36 and a distal end 38, and one or more electrodes 40, 42 mounted in or on the shaft 34 of the distal portion of catheter 16. In an exemplary embodiment, the electrodes 40, 42 are disposed at or near the distal end portion 38 of the shaft 34, with the electrode(s) 40 comprising an ablation electrode disposed at the extreme distal end portion 38 of the shaft 34 (i.e., tip electrode 40), and the electrode(s) 42 comprising a positioning electrode used, for example, with the visualization, navigation, and mapping system 20. Positioning electrode(s) 42 can be configured to provide a signal indicative of both a position and orientation of at least a portion of the catheter 16. The catheter 16 may further include other conventional components such as, for example and without limitation, a temperature sensor (or sensors) 44, additional electrodes, and corresponding conductors.

The connector 30 provides mechanical, fluid, and electrical connection(s) for cables 46, 48, 50 extending from the pump 28, the ablation system 18, and the visualization, navigation, and/or mapping system 20. The connector 30 is conventional in the art and is disposed at the proximal end 36 of the catheter 16.

The handle 32 provides a location for the clinician to hold the catheter 16 and may further provide means for steering or guiding the shaft 34 within the body 14 as known in the art. Catheter handles 32 are generally conventional in the art and it will be understood that the construction of the handle 32 may vary. In an embodiment, for the purpose of steering the shaft 34 within the body 14, the handle 32 can be substituted by a controllable robotic actuator.

The shaft 34 is an elongate, tubular, flexible member configured for movement within the body 14. The shaft 34 supports, for example and without limitation, one or more electrodes (e.g., electrodes 40, 42), associated conductors, and possibly additional electronics used for signal processing, visualization, localization, and/or conditioning. The shaft 34 may also permit transport, delivery and/or removal of fluids (including irrigation fluids, medicaments, and bodily fluids, etc.), medicines, and/or surgical tools or instruments. The shaft 34 can include one or more lumens configured to house and/or transport electrical conductors, fluids, or surgical tools. The shaft 34 can be introduced into a blood vessel or other structure within the body 14 through a conventional introducer. The shaft 34 is then steered or guided through the body 14 to a desired location such as the tissue 12 with pullwires, tension elements, so-called push elements, or other means known in the art.

As generally illustrated in FIG. 1, an ablation system 18 can be comprised of, for example, an ablation generator 52 and one or more ablation patch electrodes 54. The ablation generator 52 generates, delivers, and controls ablation energy (e.g., RF) output by the ablation catheter 16 and the tip electrode 40 thereof, in particular. The generator 52 is conventional in the art and may comprise a commercially available unit sold under the model number IBI-1500T RF Cardiac Ablation Generator, available from St. Jude Medical, Inc. In an exemplary embodiment, the generator 52 may include an RF ablation signal source 56 configured to generate an ablation signal that is output across a pair of source connectors: a positive polarity connector SOURCE (+), which electrically connects to the tip electrode 40 of the catheter 16; and a negative polarity connector SOURCE (−), can be electrically connected to one or more of the patch electrodes 54. It should be understood that the term connectors as used herein does not imply a particular type of physical interface mechanism, but is rather broadly contemplated to represent one or more electrical nodes (including multiplexed and de-multiplexed nodes). The source 56 is configured to generate a signal at a predetermined frequency in accordance with one or more user specified control parameters (e.g., power, time, etc.) and under the control of various feedback sensing and control circuitry. The source 56 may generate a signal, for example, with a frequency of about 450 kHz or greater for RF energy. The generator 52 may also monitor various parameters associated with the ablation procedure including, for example, impedance, the temperature at the distal tip of the catheter, applied ablation energy, power, force, proximity, and the position of the catheter, and provide feedback to the clinician or another component within the system 10 regarding these parameters.

The visualization, navigation, and/or mapping system 20 with which the positioning electrode 42 can be used may comprise an electric field-based system, such as, for example, that having the model name ENSITE NAVX (aka EnSite Classic as well as newer versions of the EnSite system, denoted as ENSITE VELOCITY) and commercially available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the positioning electrode(s) 42 can be configured to be responsive to an electric field transmitted within the body of the patient. The positioning electrode(s) 42 can be used to sense an impedance at a particular location and transmit a representative signal to an external computer or processor. The positioning electrode(s) 42 may comprise one or more ring electrodes in an electric field-based system. In other exemplary embodiments, however, the visualization, navigation, and/or mapping system may comprise other types of systems, such as, for example and without limitation: a magnetic field-based system such as the CARTO System (now in a hybrid form with impedance- and magnetically-driven electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by St. Jude Medical, Inc.), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the positioning electrode(s) 42 can be configured to be responsive to a magnetic field transmitted through the body of the patient. The positioning electrode(s) 42 can be used to sense the strength of the field at a particular location and transmit a representative signal to an external computer or processor. The positioning electrode(s) 42 may comprise one or more metallic coils located on or within the catheter 16 in a magnetic field-based system. As noted above, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the positioning electrodes 42 may comprise both one or more impedance-based electrodes and one or more magnetic coils. Commonly available fluoroscopic, computed tomography (CT), and magnetic resonance imaging (MRI)-based systems can also be used.

Figure 2:
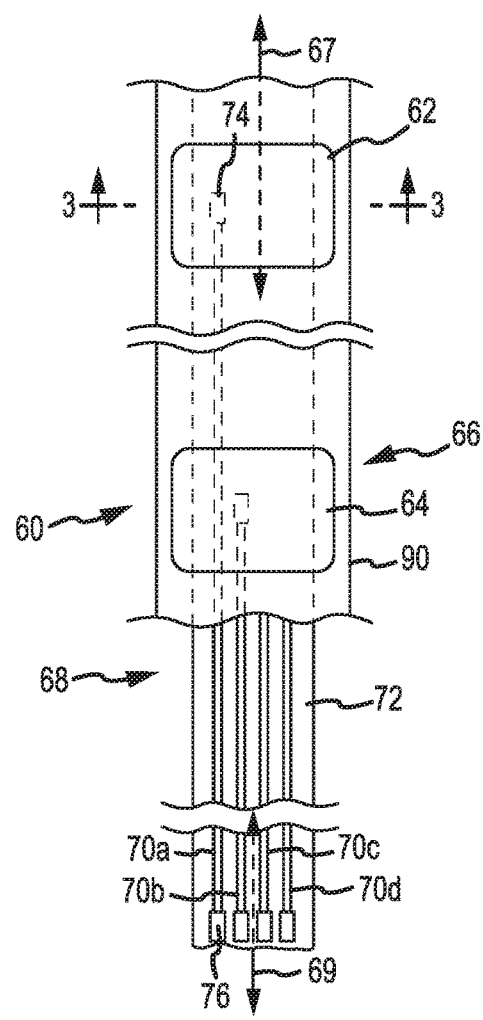
FIG. 2 is a side view of a catheter design employing a flexible circuit coupled with a plurality of electrodes.
Figure 3:
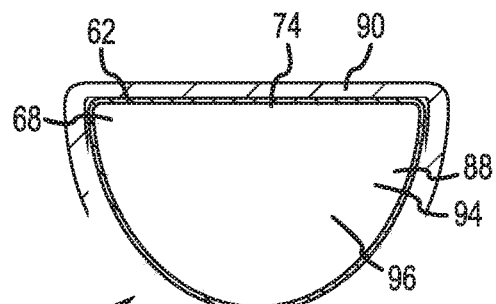
FIG. 3 is a cross-sectional view of the catheter of FIG. 2, taken along line 3-3.

FIGS. 2 and 3 illustrate the construction of an embodiment of a distal portion of a catheter 60, which can be similar to the distal portion 38 of catheter 16 generally illustrated in FIG. 1. The catheter 60 includes a shaft 66 having a proximal end and a distal end. The shaft 66 has a longitudinal axis 67. The catheter 60 may include catheter electrode assembly. The catheter electrode assembly may include a flexible circuit 68 that includes a longitudinal axis 69 and a plurality of electrical traces (e.g., traces 70a, 70b, 70c, 70d), embedded within an insulating substrate 72. Furthermore, the flexible circuit 68 may include one or more electrical pads that provide for an electrical connection with at least one of the plurality of electrical traces (e.g., traces 70a, 70b, 70c, 70d) through the substrate 72. For example, as generally illustrated in FIG. 2, electrical trace 70a may include a distally located pad 74 that can be configured to electrically couple the trace 70a with the distal electrode 62. Additionally, a proximally located pad 76 may allow a wire lead, connector, or other electrical component to couple with the trace 70a, and thereby be in electrical communication with an electrode (e.g., electrode 62). There can be a corresponding distally located pad 74 for each proximally located pad 76. The distally located pads 74 can be substantially equally spaced along the longitudinal axis 69 of the flexible circuit 68. In an embodiment, anisotropic conductive film (ACF) technology can be used to make mass electrical terminations and electrical connections with respect to the flexible circuit 68.

In an embodiment, the flexible circuit 68 can be a multi-layered circuit that provides for multiple electrical traces to be stacked or held in a matrix-type arrangement. In this respect, a flexible circuit can be comprised of a material that is capable of withstanding a high degree of elastic deformation without being prone to fracture or plastic deformation. Exemplary flexible substrates may include, without limitation, flexible plastics, such as polyimide or polyetheretherketone (PEEK) films, polyesters, polyethylene terephthalate materials and/or a combination thereof. Other flexible and/or elastic circuit technologies can be used.

In an embodiment, the thickness of an embedded trace can be varied based on the function the trace is designed to perform. For example, if the trace is intended to deliver ablative energy to the electrode, it may have a thicker profile to accommodate a greater current throughput. Likewise if the trace is configured to return a lower-current sensory signal, it may have a narrower profile. Conversely, in an embodiment, all traces may have the same cross sectional profile, however, multiple traces can be joined in parallel to accommodate greater currents.

Figure 4:
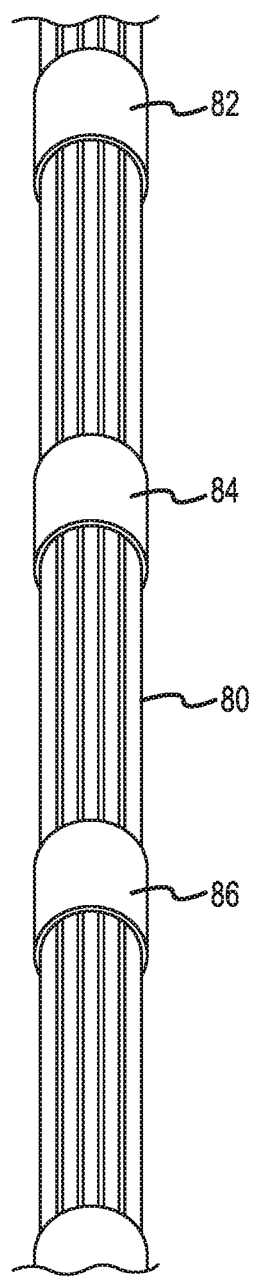
FIG. 4 is an isometric view of the top-side of a flex circuit electrode assembly.
Figure 5:
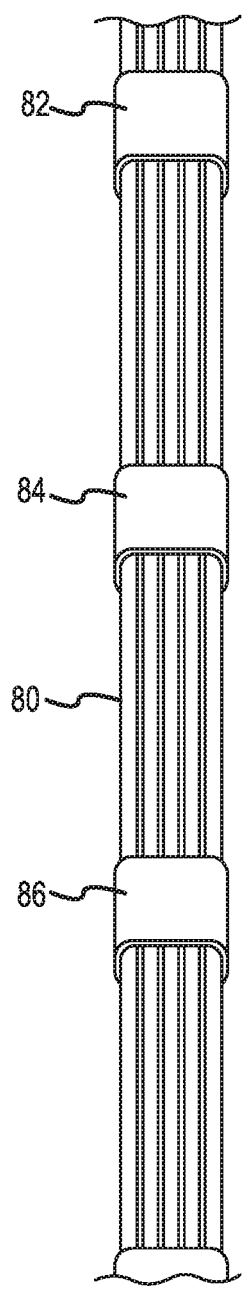
FIG. 5 is an isometric view of the bottom-side the flex circuit electrode assembly of FIG. 4.

The catheter electrode assembly may further include at least one electrode (e.g., electrode 62). The catheter electrode assembly may include a plurality of electrodes (e.g., electrodes 62, 64) that can be disposed along the longitudinal axis 67 of the shaft 66. In an embodiment, each electrode may comprise an electrically conductive material that can be generally resistant to corrosion. An exemplary electrode can be constructed from, for example, platinum, however other conductive materials known in the art may similarly be used. As generally illustrated in FIG. 3, the electrode 62 can be adjacently situated to the flexible circuit 68 in such manner as to permit electrical coupling with one or more of the electrical traces (e.g., traces 70a, 70b, 70c, 70d) through distally located electrical pads 74. In an embodiment, the electrode 62 can be a ring electrode surrounding or encircling the flexible circuit 68 and associated electrical pad 74. The electrode 62 can be mechanically fastened to the flexible circuit 68 in a manner that prevents relative movement during assembly and use. Exemplary fastening techniques may include mechanically crimping the electrode 62 to the flexible circuit 68, affixing the electrode 62 to the pad 74, and/or encapsulating the elements in a common tubing. Additionally, or via the mechanical fastening, the electrode 62 can be electrically coupled to the pad 74. The electrodes 62, 64 can be substantially equally spaced along the longitudinal axis 69 of the flexible circuit 68. Although the distally located pads 74 and electrodes 62, 64 are described as being substantially equally spaced along the longitudinal axis 69 of the flexible circuit 68 in an embodiment, the distally located pads 74 and electrodes 62, 64 may not be substantially equally spaced along the longitudinal axis 69 of the flexible circuit 68 in other embodiments. Techniques for electrically coupling the electrode 62 are know in the art, and may include, for example, laser welding, ultrasonic welding, or cold soldering. FIGS. 4 and 5 illustrate top and bottom perspective views of an exemplary flexible circuit 80 having a plurality of affixed electrodes 82, 84, and 86. The electrode 62, 64 or 82, 84, 86 can be generally D-shaped or hemi-cylindrical in accordance with an embodiment. Such D-shaped or hemi-cylindrical electrodes can be purchased and/or can be formed using an appropriately shaped crimping tool. While FIGS. 3-5 illustrate a generally "D" shaped or hemi-cylindrical electrode ring, in other embodiments, the electrode 62, 64 or 82, 84, 86 may resemble different geometries, such as having a circular appearance, or having a general kidney bean shape (e.g., having a regular and/or irregular cross-sectional shape(s)).

Referring again to FIG. 3, the catheter electrode assembly can further include a liner tube 88 extending within the electrode 62 or electrodes 62, 64. The liner tube 88 can be a hollow tube that provides a passageway or lumen for support elements, guide elements, fluids, or other known catheter components to extend through, yet be electrically isolated from electrodes 62, 64. In an embodiment, the liner tube 88 can be constructed from a material such as polytetrafluoroethylene (PTFE), which is commonly sold by the E. I. du Pont de Nemours and Company under the trade name Teflon®. In an embodiment where multiple electrodes 62, 64 or 82, 84, 86 are provided on a single flexible circuit 68 or 80 (as generally illustrated in FIGS. 3 and 4 and 5), a single liner tube 88 may extend along the entire flexible circuit 68, 80 and within each electrode 62, 64 or 82, 84, 86. In an embodiment, prior to applying the outer covering 90, a portion or all of the liner tube 88 can be etched through a chemical or laser etching process in a manner that may promote bonding with the outer covering 90.

During assembly, the liner tube 88 may first be placed over a temporary, appropriately shaped solid or hollow mandrel (not shown). The liner tube 88 and associated mandrel may then be slid along the length of the flexible circuit 68, 80, and within one or more of the affixed electrodes 62, 64 or 82, 84, 86. The mandrel aids in grasping and/or manipulating the catheter during assembly, and may further provide physical support for the catheter during this same period. Once the catheter assembly is complete, the temporary mandrel can be removed from the device.

The catheter electrode assembly can further include an outer covering 90 that forms a portion of the outer shell of the catheter 60. The outer covering 90 may comprise a polymer. In an embodiment, the outer covering 90 comprises a thin-walled heat shrinkable tubing that may extend over the flexible circuit 68 or 80, electrodes 62, 64 or 82, 84, 86, and a portion of the liner tube 88. The heat shrinkable tubing may comprise multiple layers in an embodiment. In an assembly incorporating heat shrinkable tubing as an outer covering 90, the assembly may desirably be heated to allow the outer tubing 90 to shrink and recover its pre-expanded shape. In another embodiment, the outer covering 90 can be applied by dip coating the flexible circuit 68 or 80, electrodes 62, 64 or 82, 84, 86, and liner tube 88 assembly in a polymeric dispersion coating process.

In still a further embodiment, the outer covering 90 can be formed by placing the flexible circuit 68 or 80, electrodes 62, 64 or 82, 84, 86, and liner tube 88 assembly into a thin-walled, low durometer, reflowable polymeric material. The reflowable polymeric material can comprise, for example, polyether block amides such as those sold under the trademark PEBAX® and generally available from Arkema France. In an assembly incorporating a reflowable polymer, an additional, temporary flouropolymer (FEP) heat shrinkable tube can be placed over the assembly and heated during the reflow process to promote dimensional recovery and promote bonding with the etched liner tube 88 and/or the electrode 62, 64 or 82, 84, 86. Once the reflow process is completed, the temporary FEP heat shrinkable tubing may then be removed.

Following the application of the outer covering 90, a portion of the outer covering 90 adjacent each electrode 62, 64 or 82, 84, 86 can be removed to expose the conductive electrode surface 92. In an embodiment, the polymeric outer cover material can be removed through, for example, a laser ablation process. The removal of at least a portion of the outer covering 90 can allow for the exposed conductive electrode surface 92 to be in a preferred location and/or face in a preferred direction. For example, the exposed conductive electrode surface 92 can be located opposite to the portion of the electrode 62, 64 or 82, 84, 86 that is connected to electrical pad 74 of electrical traces 70a, 70b, 70c, 70d. Accordingly, the exposed conductive electrode surface 92 may face in a direction that is opposite to the direction that the electrical pad 74 faces. In an embodiment, the exposed conductive electrode surface 92 may face away from tissue within a human body 14 (e.g., heart or cardiac tissue 12) when the catheter electrode assembly is located within a human body 14. The use of a ring electrode 62, 64 or 82, 84, 86 with an exposed conductive electrode surface 92 may increase the available surface area of each electrode. An exemplary exposed electrode surface area can be roughly 1 mm$^2$; however, smaller or larger areas can be exposed as dictated by the nature of the catheter and by the electrode's intended application. In other embodiments, the exposed conductive electrode surface 92 can be created by preventing the outer covering 90 from bonding to at least a portion of electrode 62, 64 or 82, 84, 86.

In an embodiment, a structural support member 94 and/or one or more radio opaque marker(s) 96 can be included within at least a portion of the liner tube 88. A structural support member 94 may provide axial support for the catheter (i.e., can be substantially resistant to compression), while promoting or allowing the catheter to deform away from the longitudinal axis (i.e., bend). In an embodiment, as shown in FIG. 3, the structural support member 94 can be a rectangular element comprised of a material such as NiTi (Nitinol), which exhibits an ability to accommodate large strains without plastically deforming. In another embodiment, the structural support member can be a more complex "spine," such as described, for example, in co-pending U.S. patent application Ser. No. 12/615,016, entitled "Device for Reducing Axial Shortening of Catheter or Sheath Due to Repeated Deflection," which is herein incorporated by reference in its entirety. Furthermore, one or more radio opaque marker(s) 96 can be included within the catheter to allow the catheter to be readily visible using fluoroscopy or other electromagnetic viewing systems.

The catheter electrode assembly described above with respect to FIGS. 2-5 can be employed to fabricate any number of types of catheters; however, the use of the flexible circuit technology may be specifically beneficial when constructing certain micro-catheters, such as those with a diameter of 2-3 French gauge (i.e., 0.67 mm-1.0 mm diameter).

Figure 6:
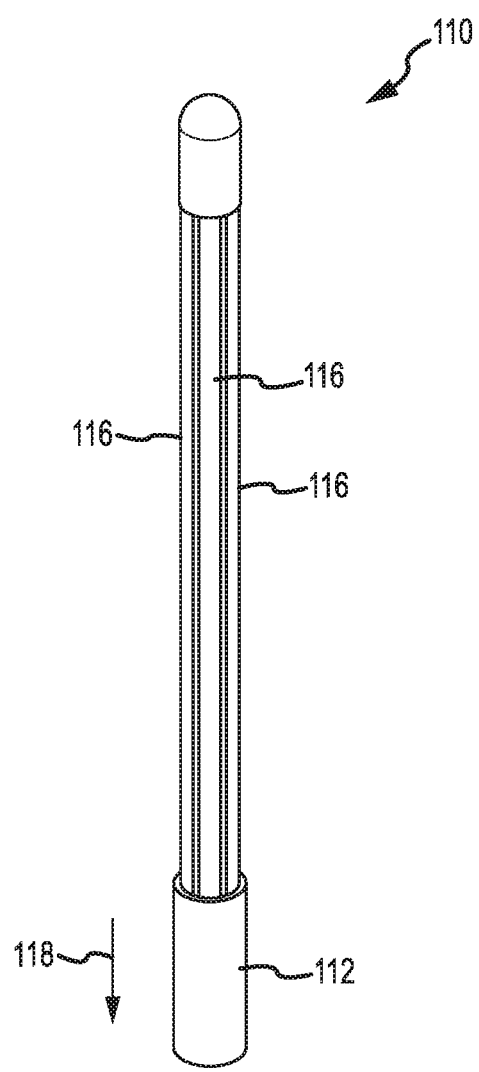
FIG. 6 is an isometric view of a noncontact electrode basket catheter in a collapsed configuration.
Figure 7:
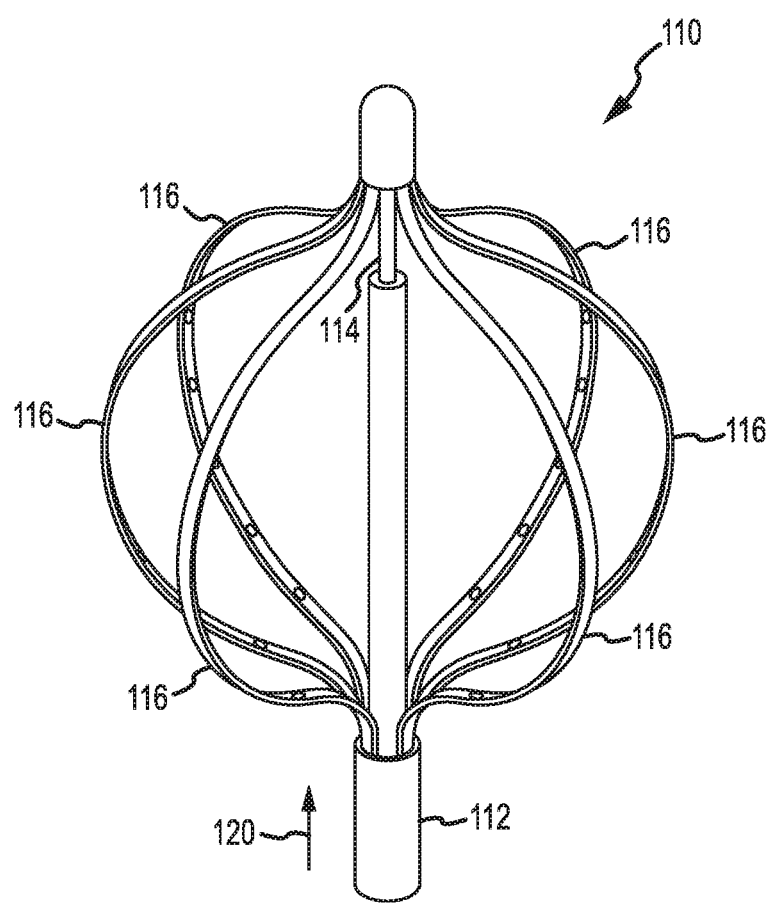
FIG. 7 is an isometric view of the noncontact electrode basket catheter of FIG. 6, shown in an expanded configuration.

In an embodiment, the catheter electrode assembly can be used to construct a plurality of splines for a non-contact electrode basket. FIGS. 6 and 7 illustrate an exemplary embodiment of a non-contact electrode basket catheter 100 which can be implemented with the catheter system 10 in FIG. 1. FIG. 6 generally illustrates the basket portion of the catheter in a collapsed configuration, and FIG. 7 generally illustrates the basket portion of the catheter in an expanded configuration. In these figures, an exemplary basket catheter 110 is shown that may include an outer tubing 112. Outer tubing 112 houses a deployment member 114 and a plurality of splines 116. An inflatable balloon or other expandable structure can be used to promote stable expansion of the basket.

In an embodiment, each spline 116 can be connected at its proximal end to the outer tubing 112, and connected at its distal, or opposite end, to the deployment member 114. The deployment member 114 is operable to be moved in a first direction (e.g., in the direction of arrow 118) relative to the outer tubing 112 to expand the splines 116 to a deployed position, as shown in FIG. 7. The deployment member 114 is also operable to be moved in a second direction (e.g., in the direction of arrow 120 in FIG. 7) relative to the outer tubing 112 to collapse the splines 116 to an undeployed position, as shown in FIG. 6. The deployment member 114 may comprise a hollow tubing and/or a pull wire in embodiments of the invention. The deployment member 114 can be sufficiently rigid such that the deployment member 114 can be operated remotely (e.g., outside of the patient's body) to be moved in the directions illustrated by arrows 118, 120 in FIGS. 6-7 to expand and contracts the splines 116. The deployment member 114 may comprise solid stainless steel or Nitinol for example.

Figure 8:
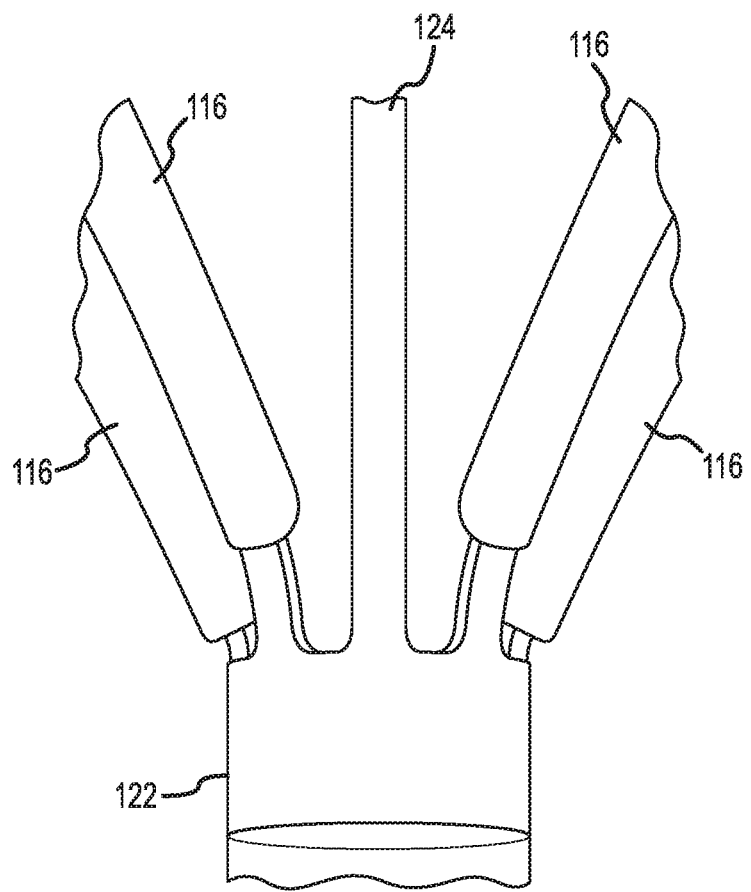
FIG. 8 is an isometric view of a plurality of catheter splines coupled with an attachment ring.

Each spline 116 may comprise a catheter electrode assembly as generally illustrated in FIGS. 2-3 or FIGS. 4-5 and described herein. As described herein, each spline 116 may comprise at least a flexible circuit 68 or 80 coupled with at least one electrode 62, 64 or 82, 84, 86. Each spline 116 may further comprise a structural support member 94. In accordance with an embodiment, the structural support member 94 of each spline 116 may comprise an individual element that can be separately connected to the outer tubing 112 and the deployment member 114. In accordance with other embodiments, the structural support members 94 of the individual splines 116 can be bonded together at one or both ends of the structural support members 94 prior to connection to the outer tubing 112 and the deployment member 114. In accordance with other embodiments, the structural support members 94 of each of the splines 116 can be formed from a common structure and can be separated into the individual structural support member 94 of each of the splines 116 while the structural support members 94 continue to share a common structure. For example, as generally illustrated in FIG. 8, the structural support member 94 of each spline 116 can be formed from a common ring 122. The common ring 122 can be separated into a plurality of protrusions (e.g., protrusions 124) extending from the common ring 122. The protrusions 124 from the common ring 122 may each act as the structural support member 94 generally illustrated in FIG. 3 for each spline 116. In an embodiment, the common ring 122 can be laser cut into a plurality of protrusions 124. Methods other than laser cutting may also be used to separate the common ring 122 into a plurality of protrusions 124 in other embodiments of the invention. The common ring 122 can be connected to the outer tubing 112 and/or the deployment member 114. The common ring 122 and the protrusions 124 can be made from Nitinol or other similarly elastic material, and may be configured for bending away from a longitudinal axis of the catheter.

Figure 9:
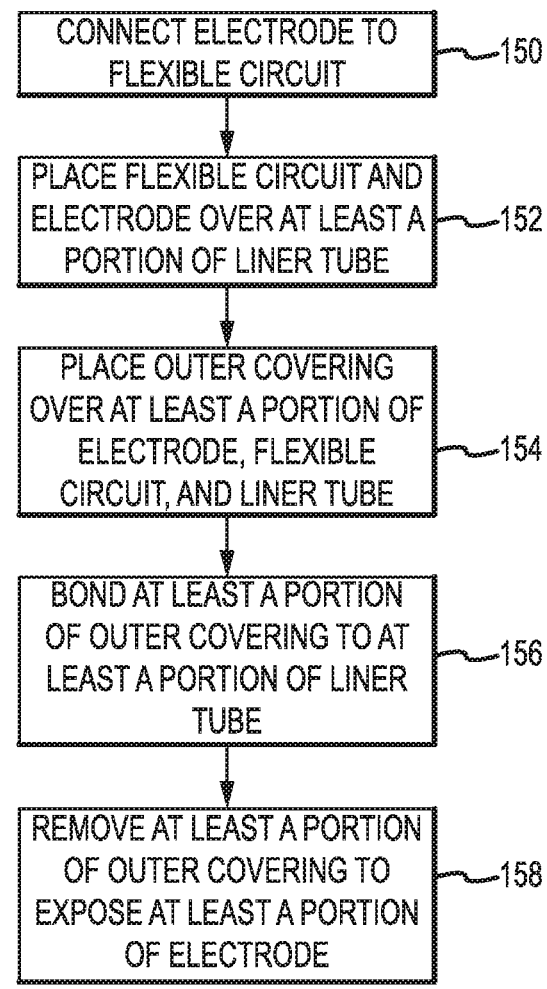
FIG. 9 is a flow diagram generally representing an exemplary method of constructing a catheter electrode assembly.

FIG. 9 is a flow diagram representing an exemplary method of constructing a catheter electrode assembly. In an embodiment of constructing the catheter electrode assembly, a mandrel can be provided. The mandrel may have a desired radial cross-sectional shape in view of the catheter electrode assembly to be made and may have a desired length in view of the catheter electrode assembly to be made. During construction, a liner tube 88 can be placed over the temporary, appropriately shaped mandrel. Once installed on the mandrel, the liner tube 88 can be secured, for example, by knotting one or both ends. In an embodiment, at least one electrode 62 is connected to a flexible circuit 68 in Step 150. The electrode 62 can be connected to the flexible circuit 68 through means such as, for example, crimping, laser welding, ultrasonic welding, or cold soldering. The flexible circuit 68 and the electrode 62 can be placed over the liner tube 88, and the temporary, appropriately shaped mandrel, in Step 152. Accordingly, the liner tube 88 and the temporary, appropriately shaped mandrel can be positioned within at least a portion of the electrode and can be positioned along the longitudinal axis of the flexible circuit. In an embodiment, the flexible circuit 68 and the electrode 62 can be placed over the liner tube 88 after the electrode 62 is connected to the flexible circuit 68. In an alternative embodiment, the flexible circuit 68 can be placed over the liner tube 88 before the electrode 62 is connected to the flexible circuit. The connection of the electrode 62 to the flexible circuit 68 may serve to hold the liner tube 88 in place.

Once the flexible circuit 68, electrode 62, and liner tube 88 are in place, in Step 154, an outer covering 90 can be placed over at least a portion of the electrode 62, at least a portion of the flexible circuit 68, and at least a portion of the liner tube 88 as formed. The outer covering 90 can comprise either a single section or alternatively multiple sections of tubing that are either butted together or overlapped with each other. The outer covering 90 may comprise any number of materials and can be any length and/or hardness (durometer) allowing for flexibility of design, as known in the art. At least a portion of the outer covering 90 may then be bonded to at least a portion of the liner tube 88 in Step 156. The process of bonding can be achieved by heat-shrinking or reflowing the outer covering 90 to the electrode 62, flexible circuit 68, and/or liner tube 88. For example, the process of bonding can be achieved by using a thin walled, multiple layer, heat shrinkable tubing for outer covering 90 can be heated to recover its shape. For another example, the process of bonding can be achieved by using a polymeric dispersion coating for outer covering 90 can be applied through a dip coating process. For a third example, the assembly thus formed (i.e., the flexible circuit 68, electrode 62, and liner tube 88) can be subjected to a reflow lamination process, which involves heating the assembly until the outer covering 90 flows and redistributes around the circumference. The formed catheter electrode assembly may then be cooled and the distal and proximal end portions of the catheter electrode assembly may then be finished in a desired fashion. In an embodiment, the outer surface of the liner tube 88 can be etched to promote bonding with the outer covering 90. Finally, in Step 158, at least a portion Although several embodiments of this invention have been described above with a certain degree of particularity, those skilled in the art could make numerous alterations to the disclosed embodiments without departing from the scope of this invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure can be made without departing from the invention as defined in the appended claims.

The invention claimed is:

1. A catheter comprising:
    an elongate shaft structure comprising a proximal portion and a distal portion;
    wherein the distal portion comprises:
        a flexible substrate;
        an electrode;
        an electrical trace coupled to the flexible substrate and the electrode; and
        a biocompatible outer covering extending over at least a portion of the flexible substrate;
        wherein the biocompatible outer covering extends over at least a portion of the electrode; and
        wherein at least a portion of the electrode is exposed by the biocompatible outer covering.

2. The catheter of claim 1, further comprising a superelastic support member electrically isolated from the electrode.

3. The catheter of claim 2, wherein the superelastic support member includes nitinol.

4. The catheter of claim 2, further comprising a common structure extending along a length of the elongate shaft structure, and wherein the superelastic support member comprises a protrusion extending from the common structure.

5. The catheter of claim 1, further comprising a nonconductive liner tube disposed within at least a portion of the electrode.

6. The catheter of claim 5, wherein the biocompatible outer covering is bonded to at least a portion of the liner tube.

7. The catheter of claim 1, wherein the electrode has an outer diameter of about 3 French gauge or less.

8. The catheter of claim 1, further comprising at least one radio opaque marker disposed within at least a portion of the electrode.

9. The catheter of claim 1, wherein the electrode comprises a ring electrode.

10. The catheter of claim 1, further comprising a plurality of electrodes disposed along the length of the flexible substrate, each electrode surrounding the flexible circuit and being electrically coupled to the electrical trace.

11. The catheter of claim 1, wherein the flexible substrate comprises polyimide, polyetheretherketone, polyester, polyethylene terephthalate material, or a combination thereof.

12. The catheter of claim 1, wherein the electrode is coupled with the electrical trace through an electrical pad.

13. The catheter of claim 1, further comprising at least one positioning electrode, wherein the at least one positioning electrode is configured to provide a signal indicative of at least one of a position and an orientation of at least a portion of the catheter by sensing an impedance.

14. The catheter of claim 1, further comprising at least one positioning electrode, wherein the at least one positioning electrode is configured to provide a signal indicative of at least one of a position and an orientation of at least a portion of the catheter by sensing a strength of a magnetic field.

15. The catheter of claim 1, further comprising a plurality of positioning electrodes, wherein at least one of the plurality of positioning electrodes is configured to provide a signal indicative of at least one of a position and an orientation of at least a portion of the catheter by sensing an impedance and wherein at least one of the plurality of positioning electrodes is configured to provide a signal indicative of at least one of a position and an orientation of at least a portion of the catheter by sensing a strength of a magnetic field.

16. A catheter including an outer tubing defining a longitudinal axis, a deployment member, and a plurality of splines, at least one of the plurality of splines comprising:
    a flexible circuit comprising an electrical trace coupled to a flexible substrate;
    an electrode electrically coupled with the flexible circuit;
    a biocompatible outer covering extending over at least a portion of the electrode; and
    a nonconductive liner tube disposed within at least a portion of the electrode;
    wherein a portion of the at least one spline is configured to deflect away from the longitudinal axis of the outer tubing when the deployment member is actuated.

17. The catheter of claim 16, wherein the flexible circuit extends along an uninterrupted length of an exterior surface of the nonconductive liner.

* * * * *